(12) United States Patent
Joseph et al.

(10) Patent No.: US 12,203,834 B1
(45) Date of Patent: *Jan. 21, 2025

(54) DISPOSABLE BIOMEMS COAGULATION PROFILING CARTRIDGE WITH A TRACKED OSCILLATING DISC

(71) Applicant: iFirst Medical Technologies, Inc., Honolulu, HI (US)

(72) Inventors: Luke B. Joseph, Honolulu, HI (US); Thomas A. Hasling, Honolulu, HI (US)

(73) Assignee: iFirst Medical Technologies, Inc., Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/462,722

(22) Filed: Sep. 7, 2023

Related U.S. Application Data

(63) Continuation of application No. 17/087,518, filed on Nov. 2, 2020, now Pat. No. 11,788,941, which is a
(Continued)

(51) Int. Cl.
*G01N 33/66* (2006.01)
*B01L 3/00* (2006.01)
(Continued)

(52) U.S. Cl.
CPC .............. *G01N 11/14* (2013.01); *B01L 3/502* (2013.01); *G01N 33/86* (2013.01);
(Continued)

(58) Field of Classification Search
CPC ... G01N 33/66; G01N 11/14; G01N 2011/147
(Continued)

(56) References Cited

U.S. PATENT DOCUMENTS 3,053,078 A   9/1962   Jewett
3,479,858 A * 11/1969  Miyake ................ G01N 11/165
                                                    374/48
(Continued)

FOREIGN PATENT DOCUMENTS

EP          0525273 B1    10/1996
JP        2001/263533      9/2001
(Continued)

OTHER PUBLICATIONS

Castro-Paacio, J.C. et al., American Journal of Physics 2013, 81, 472-475.
(Continued)

*Primary Examiner* — Arlen Soderquist
(74) *Attorney, Agent, or Firm* — Knobbe, Martens, Olson & Bear, LLP

(57) ABSTRACT

A handheld medical analyzer works with different disposable application cartridges to perform a variety of interrogations on specimen samples. One application includes attaching a biological microelectromechanical systems (BioMEMS) cartridge that generates blood coagulation profiles indicative of particular forms of coagulation disorders. The device makes coagulopathy testing simpler for small hospitals, clinics, ambulances, remote locations and individuals and permits for a larger number of parallel or serial devices operating simultaneously. One insertion of a cartridge actuates an oscillating circular motion to generate a blood coagulation profile based on a change in rotational motion as blood coagulates in a sample. Change in rotational motion is analyzed through a video camera such as in a smartphone and is plotted to show an amplitude over time. Actuation of the BioMEMS can be achieved by magnetic actuation of a motor controlled by an iPhone or a smart phone to provide a specific rotational pattern.

20 Claims, 21 Drawing Sheets

Related U.S. Application Data continuation of application No. 15/607,105, filed on May 26, 2017, now Pat. No. 10,823,743, which is a continuation of application No. 14/526,034, filed on Oct. 28, 2014, now abandoned.

(60) Provisional application No. 61/896,405, filed on Oct. 28, 2013.

(51) Int. Cl.
*G01N 11/14* (2006.01)
*G01N 33/86* (2006.01)

(52) U.S. Cl.
CPC . *B01L 2300/041* (2013.01); *B01L 2300/0803* (2013.01); *B01L 2300/0848* (2013.01); *B01L 2400/043* (2013.01); *G01N 2011/147* (2013.01); *G01N 2800/224* (2013.01); *G01N 2800/7033* (2013.01)

(58) Field of Classification Search
USPC .............................................. 422/73; 436/69
See application file for complete search history.

(56) References Cited

U.S. PATENT DOCUMENTS

| | | | |
|---|---|---|---|
| 3,501,948 A * | 3/1970 | Spitsbergen | G01N 11/10 73/54.39 |
| 3,520,659 A | 7/1970 | Steinberg et al. | |
| 3,531,996 A * | 10/1970 | Harris | G01N 11/162 374/48 |
| 3,650,698 A | 3/1972 | Adler | |
| 3,681,980 A * | 8/1972 | Decker | G01N 3/34 374/48 |
| 3,695,842 A | 10/1972 | Mintz | |
| 3,704,099 A | 11/1972 | Sanz | |
| 3,836,333 A | 9/1974 | Mintz | |
| 3,861,197 A | 1/1975 | Adler | |
| 3,875,791 A | 4/1975 | Fitzgerald et al. | |
| 4,045,999 A | 9/1977 | Palmer | |
| 4,081,242 A | 3/1978 | Girolami | |
| 4,148,216 A | 4/1979 | Do et al. | |
| 4,193,293 A | 3/1980 | Cavallari | |
| 4,317,363 A | 3/1982 | Shen | |
| 4,328,701 A | 5/1982 | Mau-Tang et al. | |
| 4,334,424 A | 6/1982 | Kepes | |
| 4,341,111 A | 7/1982 | Husar | |
| 4,498,782 A | 2/1985 | Proctor et al. | |
| 4,706,207 A | 11/1987 | Hennessy et al. | |
| 4,918,984 A | 4/1990 | Martinoli et al. | |
| 4,964,728 A | 10/1990 | Kloth et al. | |
| 5,016,469 A | 5/1991 | Henderson | |
| 5,071,247 A | 12/1991 | Markosian et al. | |
| 5,110,727 A | 5/1992 | Oberhardt | |
| 5,138,872 A | 8/1992 | Henderson | |
| 5,154,082 A | 10/1992 | Mintz | |
| 5,163,317 A | 11/1992 | Ono et al. | |
| 5,181,415 A | 1/1993 | Esvan et al. | |
| 5,217,860 A | 6/1993 | Fahy et al. | |
| 5,223,227 A | 6/1993 | Zuckerman | |
| 5,350,676 A | 9/1994 | Oberhardt et al. | |
| 5,523,238 A | 6/1996 | Varon et al. | |
| 5,629,209 A | 5/1997 | Braun et al. | |
| 5,777,215 A | 7/1998 | Calatzis et al. | |
| 5,789,664 A | 8/1998 | Neel et al. | |
| 6,016,712 A | 1/2000 | Warden et al. | |
| 6,103,196 A | 8/2000 | Yassinzadeh et al. | |
| 6,136,271 A | 10/2000 | Lorincz et al. | |
| 6,165,795 A | 12/2000 | Mize et al. | |
| 6,225,126 B1 | 5/2001 | Cohen et al. | |
| 6,573,104 B2 | 6/2003 | Carr et al. | |
| 6,586,259 B1 | 7/2003 | Mahan et al. | |
| 6,591,663 B1 | 7/2003 | Murray et al. | |
| 6,591,664 B2 | 7/2003 | Litton | |
| 6,613,573 B1 | 9/2003 | Cohen | |
| 6,767,511 B1 | 7/2004 | Rousseau | |
| 6,898,532 B1 | 5/2005 | Toh et al. | |
| 6,989,272 B1 | 1/2006 | Savion et al. | |
| 7,179,652 B2 | 2/2007 | Cohen et al. | |
| 7,182,913 B2 | 2/2007 | Cohen et al. | |
| 7,211,438 B2 | 5/2007 | Toh et al. | |
| 7,235,213 B2 | 6/2007 | Mpock et al. | |
| 7,262,059 B2 | 8/2007 | Zheng et al. | |
| 7,399,637 B2 | 7/2008 | Wright et al. | |
| 7,422,905 B2 | 9/2008 | Clague et al. | |
| 7,439,069 B2 | 10/2008 | Nippoldt et al. | |
| 7,524,670 B2 | 4/2009 | Cohen et al. | |
| 7,732,213 B2 | 6/2010 | Cohen et al. | |
| 7,754,489 B2 | 7/2010 | Cohen | |
| 8,076,144 B2 | 12/2011 | Cohen | |
| 8,211,381 B2 | 7/2012 | Ricci | |
| 8,322,195 B2 | 12/2012 | Glauner et al. | |
| 8,365,582 B2 | 2/2013 | Sakai | |
| 8,383,045 B2 | 2/2013 | Schubert et al. | |
| 8,425,840 B2 | 4/2013 | Hosokawa | |
| 8,448,499 B2 | 5/2013 | Schubert et al. | |
| 8,450,078 B2 | 5/2013 | Dennis et al. | |
| 8,795,210 B2 | 8/2014 | Talish et al. | |
| 8,877,710 B2 | 11/2014 | Johansson et al. | |
| 9,046,512 B2 | 6/2015 | Djennati et al. | |
| 9,063,161 B2 | 6/2015 | Dennis et al. | |
| 10,184,872 B2 | 1/2019 | Sakai | |
| 10,739,239 B1 | 8/2020 | Joseph et al. | |
| 10,823,743 B1 | 11/2020 | Joseph et al. | |
| 11,598,707 B1 | 3/2023 | Joseph et al. | |
| 11,788,941 B1 * | 10/2023 | Joseph | B01L 3/502 435/13 |
| 2001/0022948 A1 | 9/2001 | Tuunanen | |
| 2002/0124634 A1 | 9/2002 | Litton | |
| 2002/0168294 A1 | 11/2002 | Carr et al. | |
| 2003/0064505 A1 | 4/2003 | Harttig | |
| 2003/0064507 A1 | 4/2003 | Gallagher et al. | |
| 2003/0069702 A1 | 4/2003 | Cohen et al. | |
| 2003/0073244 A1 | 4/2003 | Cohen et al. | |
| 2003/0131500 A1 | 7/2003 | Kline et al. | |
| 2003/0180824 A1 | 9/2003 | Mpock et al. | |
| 2003/0199428 A1 | 10/2003 | Carr | |
| 2004/0131500 A1 | 7/2004 | Chow | |
| 2004/0161855 A1 | 8/2004 | Kvasnik et al. | |
| 2004/0203163 A1 | 10/2004 | Cohen et al. | |
| 2004/0224419 A1 | 11/2004 | Zheng et al. | |
| 2005/0180886 A1 | 8/2005 | Bote Bote | |
| 2005/0233460 A1 | 10/2005 | Clague et al. | |
| 2005/0233466 A1 | 10/2005 | Wright et al. | |
| 2005/0255601 A1 | 11/2005 | Nippoldt et al. | |
| 2006/0034734 A1 | 2/2006 | Schubert et al. | |
| 2007/0059840 A1 | 3/2007 | Cohen et al. | |
| 2007/0158246 A1 | 7/2007 | Davies et al. | |
| 2007/0184508 A1 | 8/2007 | Cohen et al. | |
| 2007/0291345 A1 | 12/2007 | Kumar et al. | |
| 2008/0011107 A1 | 1/2008 | Leventhal et al. | |
| 2008/0015477 A1 | 1/2008 | Talish et al. | |
| 2008/0038828 A1 | 2/2008 | Cohen et al. | |
| 2008/0206880 A9 | 8/2008 | Clague et al. | |
| 2008/0233554 A1 | 9/2008 | Sehgal et al. | |
| 2008/0261261 A1 | 10/2008 | Grimes et al. | |
| 2008/0294068 A1 | 11/2008 | Briggs et al. | |
| 2009/0198120 A1 | 8/2009 | Gurbel | |
| 2009/0304547 A1 | 12/2009 | Werner et al. | |
| 2010/0139375 A1 | 6/2010 | Johns et al. | |
| 2010/0154520 A1 | 6/2010 | Schubert et al. | |
| 2010/0170327 A1 | 7/2010 | Glauner et al. | |
| 2010/0184201 A1 | 7/2010 | Schubert et al. | |
| 2010/0267066 A1 | 10/2010 | Hosokawa et al. | |
| 2010/0268094 A1 | 10/2010 | Hasling et al. | |
| 2011/0036150 A1 | 2/2011 | Sakai | |
| 2011/0151491 A1 | 6/2011 | Dennis et al. | |
| 2011/0223663 A1 | 9/2011 | Sehgal et al. | |

(56) References Cited

U.S. PATENT DOCUMENTS

| | | |
|---|---|---|
| 2011/0268732 A1 | 11/2011 | Johansson |
| 2012/0028342 A1 | 2/2012 | Ismagilov et al. |
| 2012/0111097 A1 | 5/2012 | Sierro |
| 2012/0294767 A1 | 11/2012 | Viola et al. |
| 2013/0195722 A1 | 8/2013 | Mitchell et al. |
| 2013/0267017 A1 | 10/2013 | Dennis et al. |
| 2014/0020475 A1 | 1/2014 | Inoue et al. |
| 2014/0047903 A1 | 2/2014 | Sakai |
| 2014/0273249 A1 | 9/2014 | Yuan et al. |
| 2015/0024473 A1 | 1/2015 | Wu et al. |
| 2015/0118691 A1 | 4/2015 | De Laat et al. |
| 2015/0226725 A1 | 8/2015 | Gill et al. |
| 2015/0253343 A1 | 9/2015 | Pearce et al. |
| 2015/0301018 A1 | 10/2015 | Dayel et al. |
| 2015/0304555 A1 | 10/2015 | Ehrenkranz |
| 2015/0305681 A1 | 10/2015 | Nadkarni |
| 2017/0010205 A1 | 1/2017 | Hayashi et al. |
| 2017/0283845 A1 | 10/2017 | Holmes et al. |
| 2019/0219490 A1 | 7/2019 | Hosokawa |
| 2021/0302412 A1 | 9/2021 | Joseph |
| 2023/0086165 A1 | 3/2023 | Joseph |

FOREIGN PATENT DOCUMENTS

| | | |
|---|---|---|
| KR | 101460673 | 11/2014 |
| WO | WO 2013/067536 | 5/2013 |
| WO | WO 2015/073941 | 5/2015 |
| WO | WO 2020/023726 | 1/2020 |
| WO | WO 2021/154995 | 8/2021 |

OTHER PUBLICATIONS

Crocker, J. C. et al., Journal of Colloid and Interface Science 1996, 179, 298-310.
Gasull, A. et al., IEEE 1992, 1948-1949.
"GPU-accelerated video proccessing on Mac and iOS", Sunset Lake Software, www.sunsetlakesoftware.com/2010/10/22/gpu-accelerated-video-processing-mak-and-ios; Oct. 22, 2010.
Hortschitz, W. et al, IEEE Sensors Journal 2011, 11, 2805-28-12.
International Search Report; PCT/US2019/043400; Oct. 2, 2019; 13 Pages.
Muller, O. et al., Macromolecues 1991, 24, 3111-3120.
Shore-Lesserson, L. et al., Anesthesia & Analgesia 1999, 88, 312-319.
Smith, Z. J. et al., PLOS One 2011, 11, paper e17150, 11 pages.
StirBars.com, "Stir Bar Price List" accessed Apr. 14, 2015 in 13 pages (http://www.stirbars.com/magnetic-stirbar-prices.htm).
Ziemann, F. et al, Biophysical Journal 1994, 66, 2210-2216.
Invitation to Pay Additional Fees, PCT/US2021/015491; Apr. 9, 2021; 3 pages.
International Search Report; PCT/US2021/015491; Jun. 28, 2021; 16 Pages.
Extended European Search Report for 21747890.8 mailed May 31, 2024 in 8 pages.
Anonymous: "Rhea-Line Oscillating Disc Rheometer", 2013, XP093158464, Retrieved from the Internet: URL:https://www.prescott-instruments.com/wp-contenVu ploads/201 5/09/Rheoline-ODR.pdf [retrieved on May 2, 2024].

* cited by examiner

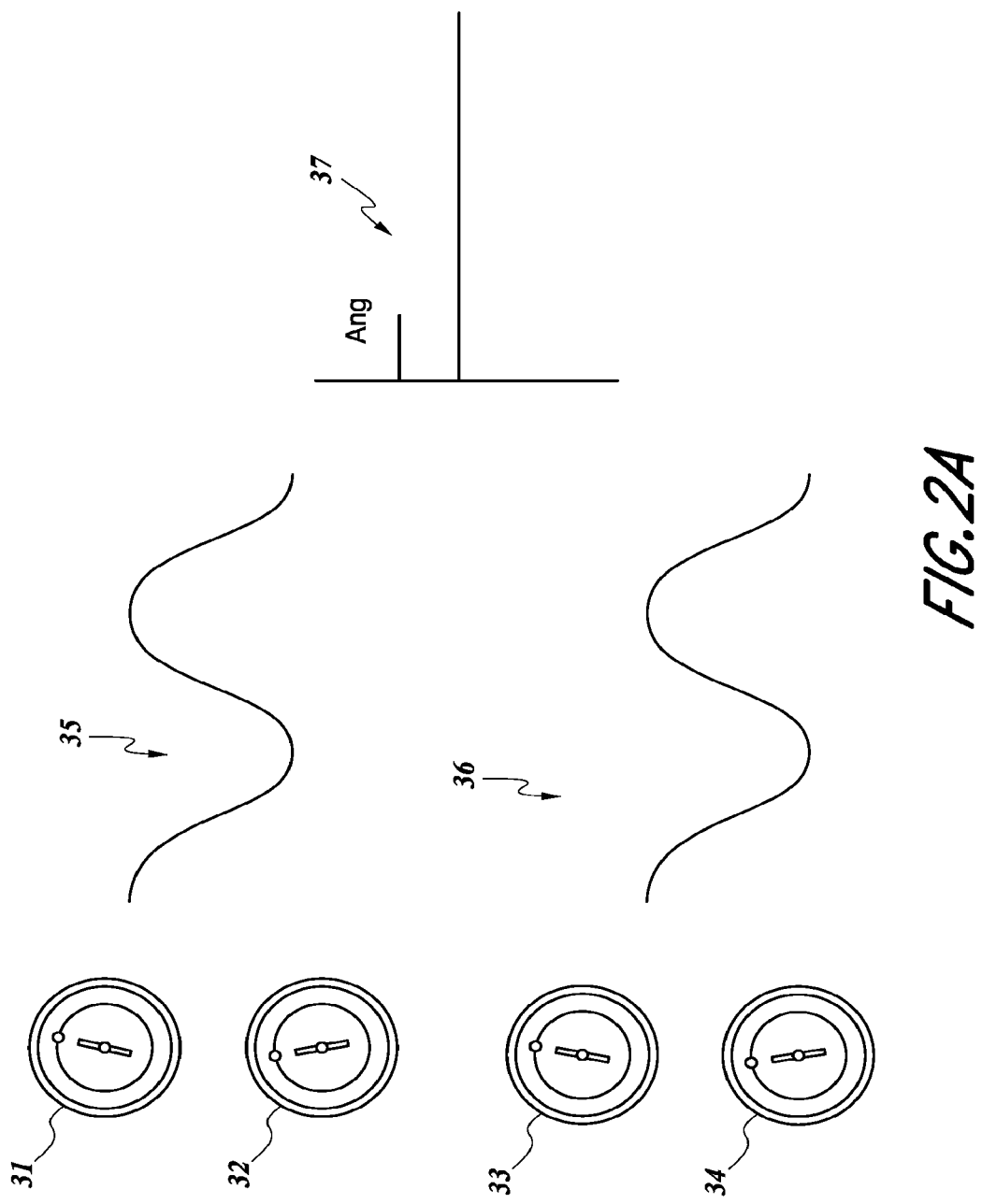

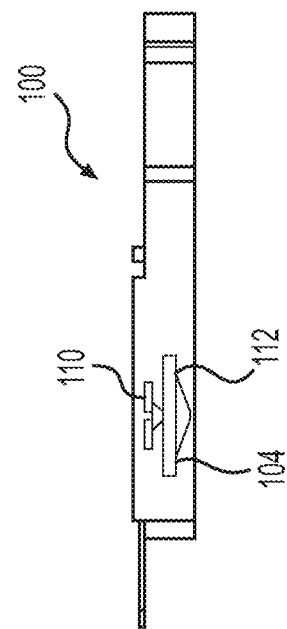
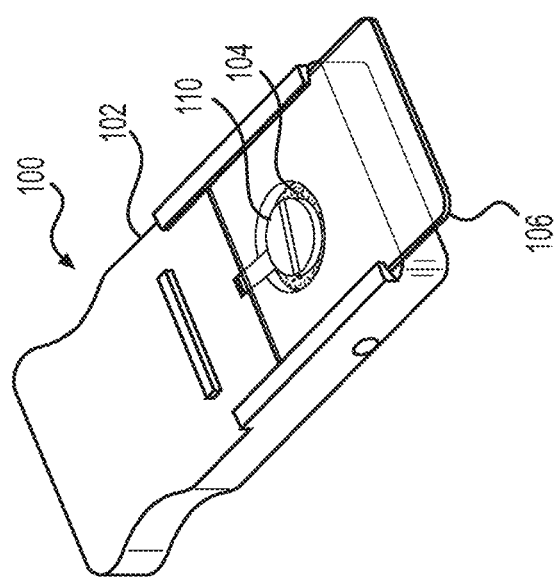
FIG. 12B
FIG. 12A

DISPOSABLE BIOMEMS COAGULATION PROFILING CARTRIDGE WITH A TRACKED OSCILLATING DISC

This application claims the benefit as a continuation of U.S. patent application Ser. No. 17/087,518 filed on Nov. 2, 2020, which is in turn a continuation of U.S. patent application Ser. No. 15/607,105 filed on May 26, 2017, which is in turn a continuation of U.S. patent application Ser. No. 14/526,034 filed on Oct. 28, 2014, which in turn claims the benefit of U.S. Provisional Application No. 61/896,405 filed Oct. 28, 2013, each of the foregoing applications of which are hereby incorporated by reference in its entirety as if fully set forth herein.

This invention was made with government support under Contract No. W81XWH-11-C-0055 awarded by the U.S. Army Medical Research Acquisition Activity. The government has certain rights in the invention.

BACKGROUND OF THE INVENTION

Five million people around the world die of trauma on an annual basis. Up to 20% of these deaths are preventable with better control bleeding. In these types of traumatic injury, the incidences of coagulation abnormalities are high. For example, natural supplies of proteins such as Factor VII are quickly depleted after trauma, which can quickly lead to hemorrhage-related death. Detecting these abnormalities quickly after the trauma often can be a predictor of the patient's mortality. These diagnostics can be a decision aid for providers and provide feedback for lifesaving actions, such as transfusions.

Although techniques such as prothrombin time (PT) and partial thromboplastin time (PTT) can test coagulation, only the first state of coagulation and plasma hemostasis are tested rather than coagulocompetence. In addition it has been shown that PT and PTT tests do not predict coagulation abnormalities as effectively as coagulation profiles, such as thrombelastography (TEG) shown in FIG. 10. In addition, separating the plasma complicates the blood processing and adds steps to the coagulation initiation.

Other coagulation profiling techniques such as thrombelastography and rotational thromboelastometry (ROTEM) shown in FIG. 10 provide a more complete coagulation profile by using whole blood. The use of whole blood includes the role of platelets, blood factors and phospholipids in the coagulation cascade. Unfortunately both standard coagulation tests (PT, PTT, etc.), and newer systems such as TEG and ROTEM, require relatively large equipment, controlled conditions and trained technicians to perform tests. These limitations prevent these diagnostic tools from being at the point of injury (POI).

In order to most effectively treat traumatic injuries, it is critical to diagnose coagulation abnormalities at the POI, ideally by first responders such as paramedic and emergency medical technicians (EMT) (FIG. 9). Paramedics and EMT's could rapidly evaluate the coagulopathy and obtain guidance in using blood products or administration of coagulation related drugs. In addition, further integration of other coagulation relevant assays, such as complete blood count (CBC) or hematocrit (HTC), base deficit, platelet count, and $PaO_2$ with a TEG-like profile could be an invaluable addition to point-of-care diagnostics.

Needs exist for improved base medical analysers and coagulation profilers.

SUMMARY OF THE INVENTION

The invention solves the existing problems by providing disposable cartridges for new base medical analysers and coagulation profiles. That can be available to be quickly used.

A primary device of the invention is a new cartridge based biological microelectromechanical system (BioMEMS) that rotates back and forth in a circular motion in direct contact to a blood sample, while the blood coagulates. This rotation changes over time as the blood coagulates in the sample. The change in motion is analyzed through a video camera (in one case an iPhone camera) and then is plotted to show an amplitude over time. The plot of motion over time is indicative of particular forms of coagulation disorders. The rotating motion of the BioMEMS device is induced externally using a magnetic field. The rotation induced is not limited to a magnetic field but could be direct mechanical or electrostatic inducer of the rotation. The magnetic actuation is provided by a motor, servo or similar device that turns a magnet. The motor can be controlled mechanically or electronically, by the iPhone for example, to provide a specific pattern. In one case the pattern is 4°45' in 5 seconds. There can be a large range of patterns, dependent on application. In one case the profile is measured for 30 to 60 minutes, however time may vary depending on application.

The invention is useful to small hospitals, clinics, ambulances, home and individuals and is useful for paramedics and EMT's.

Use of a mobile device, such as an iPhone and the new device has been demonstrated to show coagulation over time in the form of a coagulation profile. The invention makes the testing simpler by use of a cartridge and provides a method of having a large number of sequential tests to monitor a patient from POI to the emergency room (ER), operating room and recovery. The overall system and the cartridge are very small. The use of cartridges in the invention simplifies the process as compared to conventional techniques. Being small and portable there is potential provided by the invention for a large number of parallel or serial devices operating simultaneously.

The system comprises a handheld medical analyzer platform, which works with different disposable application cartridges to perform a variety of interrogations on specimen samples. One application includes attaching a biological microelectromechanical systems (BioMEMS) cartridge that generates blood coagulation profiles indicative of particular forms of coagulation disorders. The device makes coagulopathy testing simpler for small hospitals, clinics, ambulances, remote locations and individuals by use of a cartridge and permits for a larger number of parallel or serial devices operating simultaneously. One insertion of a cartridge actuates an oscillating circular motion to generate a blood coagulation profile based on a change in rotational motion as blood coagulates in a sample. Change in rotational motion is analyzed through a video camera such as in a smartphone and is plotted to show an amplitude over time. Actuation of the BioMEMS can be achieved by magnetic actuation of a motor controlled by an iPhone or a smart phone to provide a specific rotational pattern.

The present invention has a cartridge configured for inserting in a receiver to measure rate of coagulation of a liquid. A well in the cartridge is configured to receive and hold the liquid. A disk is configured for relatively rotating in the liquid within the well and is rotatable in the well, the disk or the well being relatively rotatable as the liquid coagulates.

The cartridge is configured to be inserted into a reader. The cartridge is wider than thick and longer than wide and is configured for longitudinally inserting in the receiver. The disk has a thin thickness relative to a wide diameter for fitting in the well, and the disk has a downward extending central spindle for contacting a bottom of the well. The disk has a magnetic portion for turning with a contactless magnetic coupling.

The cartridge further has a slidable lid. The disk is attached to the lid, and the cartridge has an abutment configured for abutting and detaching the disk from the lid and thereby dropping the disk into the well upon sliding the lid with respect to a remainder of the cartridge. The cartridge is configured to receive and hold blood in the well.

The present invention has a cartridge configured for inserting in a receiver and receiving a fluid sample. The cartridge has a platform. A retainer is connected to the platform for retaining the cartridge in the reader. A well in the platform holds a blood sample. A channel is embedded into the cartridge for injecting the fluid sample into the well. In one iteration the sample is injected into the channel after insertion of the cartridge into the receiver and the cartridge being brought to the desired temperature. At this point the lid is horizontally engaged and the disk is abutted to the abutment, dropping the disk into the filled well. A disk is configured to be positioned and supported in the well and to be turnable within the well. The disk further has a permeable part for magnetic coupling to a reciprocally turning magnet.

The platform has a portion configured for extending outward from the reader. The guide has a passageway in the platform connected between the well and an entrance port on the portion of the platform extending outward from the platform. The passageway slopes downward and inward from the entrance to the well. Upward and inward facing channels are situated on opposite side edges of the platform. A lid is slidable within the channels for covering the well.

The platform is constructed in two parts, an outer part and an inner part. The outer part has the portion extending out of the receiver, the guide channels for the lid and the retainer. The inner part has the well. The lid projects forward into the receiver from the cartridge when the cartridge is placed in the receiver. The disk is temporarily attached to the lid, and the platform has an abutment which contacts the disk and detaches the disk from the lid when the lid moves onward over the platform and the disk is aligned with the well.

A method of analyzing coagulation of a liquid provides a cartridge with a platform. A well is provided in the platform. A magnet is provided in the disk. A disk turns in the well, supplying the liquid in the well and reciprocally turning the disk within the liquid in the well with a magnetic coupling.

A retainer on the platform retains the platform in a receiver. An extended portion of the platform provides an entrance port for the liquid on the extended portion, and a passageway for the liquid from the entrance to the well.

The platform has upward and inward facing channels. A lid extends between and slides in the channels.

The disk is attached to the lid. The lid is extended from the platform. The lid is slid on the platform. An abutment on the platform encounters the disk on the lid, dislodging the disk from the lid, and dropping the disk into the well as the lid is slid on the platform.

The platform is inserted with the extended lid into the receiver. The liquid is injected into the entrance. The liquid flows through the passageway into the well. A pusher slides the lid and the disk drops into the well. The disk is reciprocally rotated with a non-contact magnetic coupling. Later, the cartridge is withdrawn with the platform, the disk in the well and the lid on the platform and discarding the cartridge, the platform, disk and lid.

These and further and other objects and features of the invention are apparent in the disclosure, which includes the above and ongoing written specification, with the claims and the drawings.

BRIEF DESCRIPTION OF THE DRAWINGS

FIG. 2A are images describing translation of device motion into zero amplitude profile.

FIGS. 12A and 12B are perspective and a schematic side view showing a cartridge, platform, well, extended lid, an abutment on the platform and a disk attached to the lid, all of which are inserted in a receiver after fluid is injected into the well.

DETAILED DESCRIPTION OF THE INVENTION

Figure 1A:
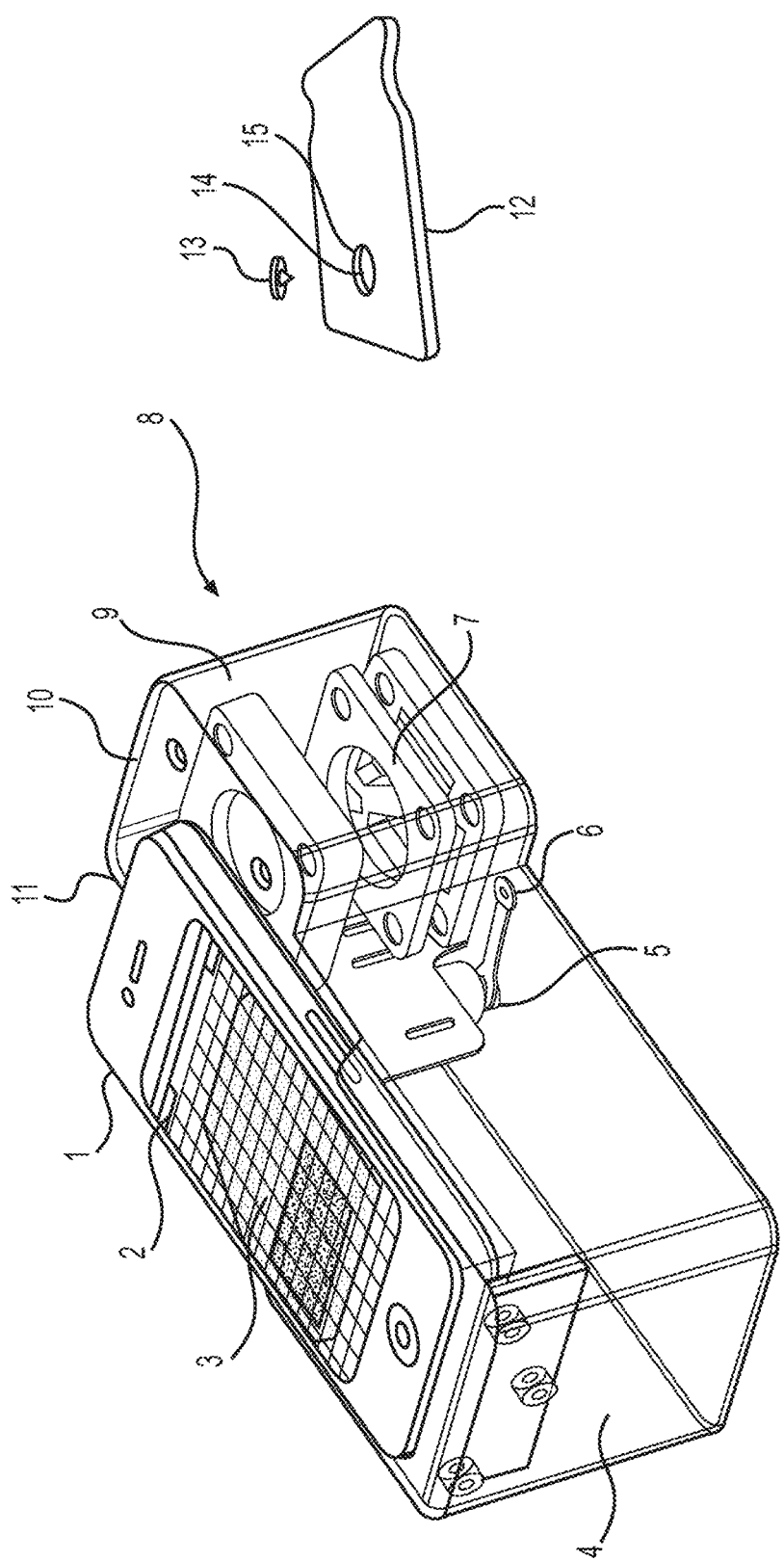
FIG. 1A is a CAD rendering of the new Coagulation Profiler and subsystems.

The invention provides a handheld medical analyzer platform and biological microelectromechanical systems (BioMEMS) cartridges. This combined system uses microfluidics, optics, a mobile device (e.g. a smartphone or tablet) and video analysis software to create a handheld analyzer that produces data used in medical and biological diagnostics. In this embodiment two primary components are the handheld medical analyzer and the coagulation profile cartridge. The combination of the handheld analyzer and coagulation profile cartridge provide results equal to bench top systems used in hospitals, such as TEG and ROTEM. The handheld medical analyzer is a platform that is capable of analyzing a variety of cartridges. However the coagulation profile cartridge is specific to coagulopathy applications only. Although the cartridges are intended to be disposable, they also can be implemented in a permanent fashion when cleaned properly and constructed of the proper material. Combined, the handheld medical analyzer and coagulation profile cartridge produce a coagulation profile which is displayed and stored on the analyzer. In this embodiment of the invention, the cartridge provides data used in diagnosing different forms of coagulopathy.

Although the combination of the handheld analyzer and coagulation profile cartridge is one part of the invention, the handheld analyzer is not limited to analyzing this specific cartridge.

Other similar embodiments include profiling the coagulation of Limulus amebocyte lysate (LAL). In this case the extent of LAL coagulation would be representative of the presence of gram negative bacteria, since the LAL reacts with bacterial endotoxin or lipopolysaccharide (LPS).

A similar cartridge would also apply to other assays that detect a physical change in the sample, such a viscosity, elasticity or viscoelasticity. Examples of these embodiments may include saliva, cervical mucus or other body fluids.

Furthermore the handheld analyzer is also capable of using the same basic configuration to analyze a great many cartridges. These embodiments would also capture data using the video camera and interrogated using the CPU and GPU running proprietary software. These cartridges include, but are not limited to $PaO_2$, pH and blood type.

Likewise similar use of a smartphone for cartridge analysis is not limited to video input, but also could use many other sensors on the smartphone, including direct electrical signals, wireless signals, manometer, accelerometer, gyroscopes and compass. This includes combinations of the different methods of obtaining direct sensor information and indirect supplementary sensor information. An example of this would be using the combined system to provide a coagulation profile, while using the smartphone, wireless communication, accelerometers, gyroscopes, GPS, etc. to provide stabilization in rough environments such as a helicopter which is in motion and vibrating. These subsystems could also be used to send the coagulation profile, GPS coordinates to the ER providing an estimated time of arrival (ETA) and allowing for preparation of blood products, etc., in advanced for the patient's arrival.

A primary embodiment of the combined inventions is shown in FIG. 1A. The coagulation profile cartridge 12 is inserted into the cartridge slot 7 where the BioMEMS device motion interfaces with the sample 15 and the motion is captured using the smartphone 1 video camera 11 and is analyzed using the smartphone central processing unit (CPU), graphics processor unit (GPU) running proprietary software. The resultant coagulation profile 3 is displayed 2 on smartphone 1 (e.g. iPhone) screen along with the measured parameters, similar to TEG/ROTEM, Table 1, Table 2. A custom enclosure 4 provides a docking point for the smartphone and attachment of peripheral components. In this embodiment the peripheral components consist of a motor 5, mechanical linkage 6 and compact microscope assembly 8, light source 9 and temperature control unit 10. The motor and linkage can be replaced with a servo and gearing, to provide the desired rotational actuation.

The coagulation profile cartridge 12 is interrogated using the compact microscope 8 and video camera 11.

Figure 1B:
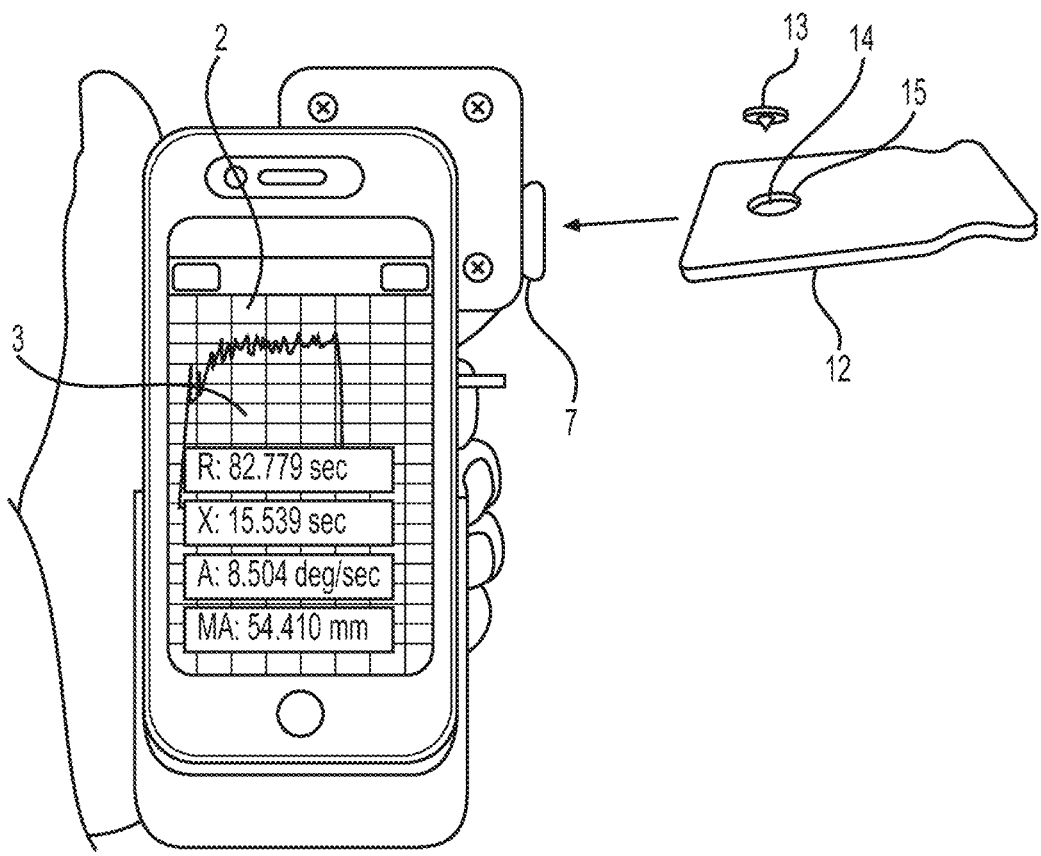
FIG. 1B is a prototype showing blood placed on cartridge is loaded into the analysis slot.

The loading protocol for the simplest embodiment of the combined system is: place blood 15 into well 14 on cartridge 12 and load the cartridge into analysis slot 7, also shown in FIG. 1B. The disc 13 may be removed prior to filling the well 14, or the well may be filled with the disc in place. In this simple embodiment the well would be filled using a pipette.

Figure 1C:
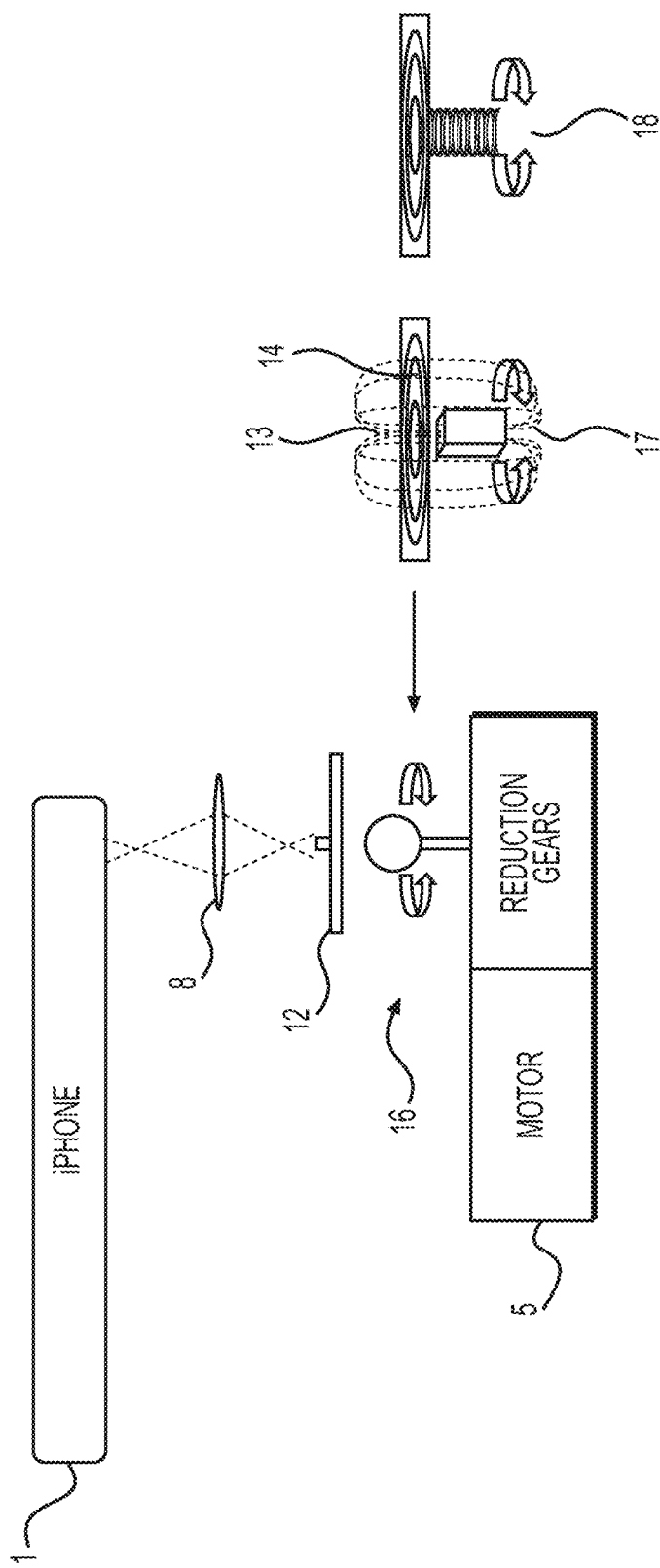
FIG. 1C is a conceptual rendering of cartridge actuation and sub system.

Upon loading the cartridge the measurement begins as the disk is actuated, as shown in FIG. 1C. Actuation in this embodiment is performed using a motor 5, mechanical linkage 6 in the form of reduction gears and magnet 16, which couples motion to the cartridge disc 13. Other embodiments would include electromagnetic induction or direct mechanical drive via a spring. By embedding ferrous metal into the cartridge disc 13, the magnetic field 17 couples the disc with the magnet. This coupling forms a link analogous to a torsion spring 18. Motion is thereby induced into the disc by rotating the magnet. In this embodiment the rotation is ±4°45' degrees over 10 seconds. Other embodiments would include any number variations in the angular rotation over time.

Figure 1D:
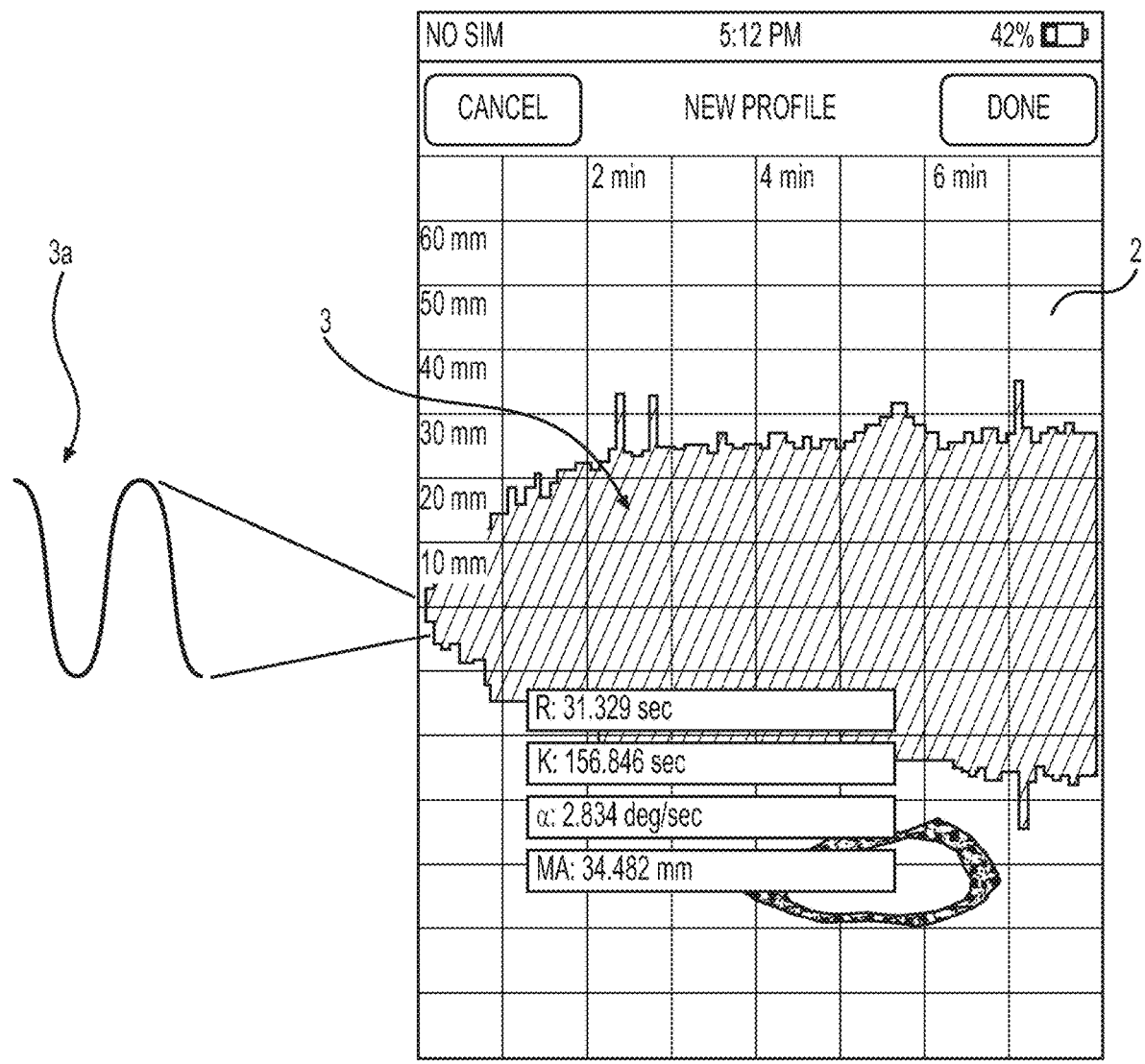
FIG. 1D is a description of displayed profile, relative to cartridge actuation.

In the embodiment the degree to which the motion is decoupled is representative of the displayed 2 profile 3, as shown in FIG. 1D. Both processed profiles 3 and preprocessed traces are sinusoidal waveforms, e.g. 3a, that represent the motion or decoupled motion. The sinusoidal waveform is acquired using the video camera and the CPU and GPU running proprietary software.

Figure 1E:
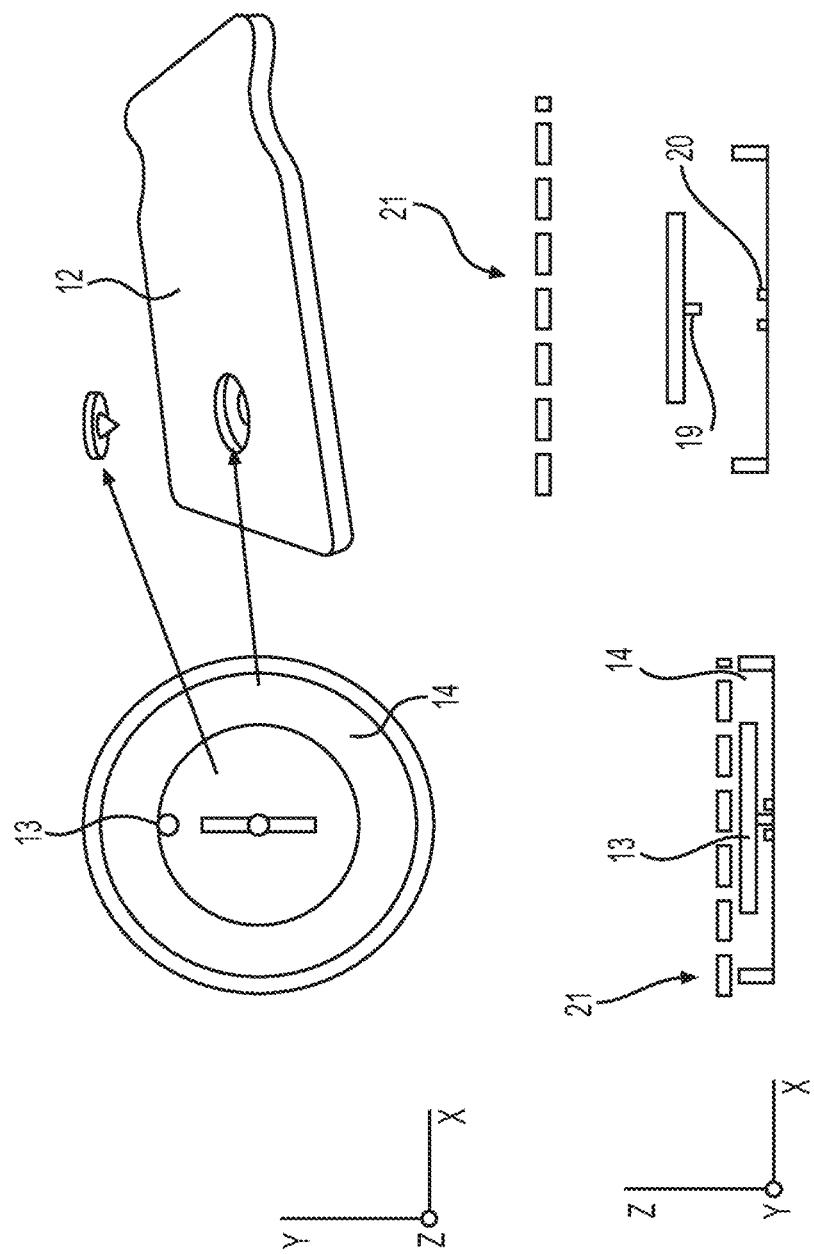
FIG. 1E is a detailed description of BioMEMS coagulation profile cartridge.

The alpha numeric displays:
R: 31.329 sec
K: 156.846 sec
a: 2.834 deg/see
MA: 34.482 mm FIG. 1E shows a cartridge 12, an enlarged well top view, side cross section and an exploded side cross section. As shown in FIG. 1E, the cartridge has a well 14 and a disc 13. The disc is seated in the well via a spindle 19 and a bearing cup 20, at the bottom of the well. Both the well and the disc are sealed in the cartridge with a clear plastic lid 21. The lid can be hinged, sliding to allow sample insertion, or a microfluidic channel maybe used to load the sample into the well. This particular subcomponent of the cartridge may be realized in a number of different embodiments. These range from a simple hole in the lid to more complex automated microfluidics channels and chambers which meter the appropriate amount of blood or reagent into the well. Likewise the insertion of the sample may range from manually using a pipette to the use of automated microfluidics.

Figure 1F:
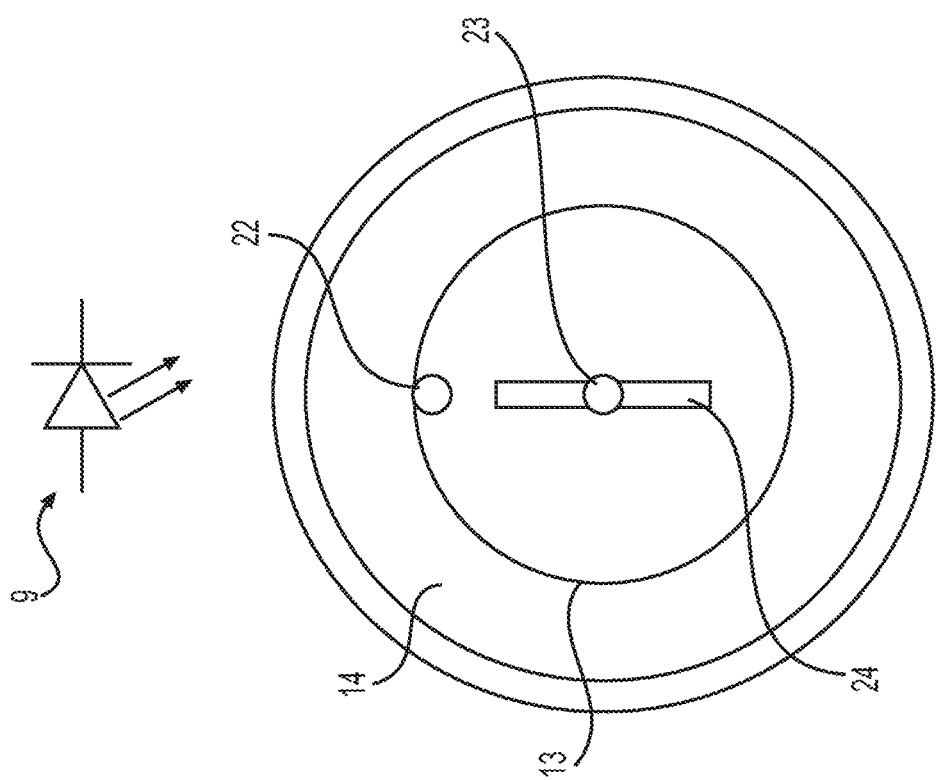
FIG. 1F is an image describing BioMEMS device marking relative to tracking.

The motion of the disc is captured by tracking two points overtime. FIG. 1F shows the pivot point 23 at the center of the disc 13 and a tracking point 22 at the outside edge of the disc. Each point is a unique color. In this embodiment the colors are florescent when illuminated using a UV LED light source 9. Both points are tracked by selecting the color to be tracked on the smartphone screen followed by selecting a threshold for the hues of the selected color to be included. The centroid of each of the prescribed points is then calculated to determine the exact location to be tracked. The angular motion is then calculated by comparing the centroid of the pivot point 23 to the centroid of the tracking point 22.

This calculation is performed real-time and is used to calculate the displayed profile continuously over time.

Figure 2B:
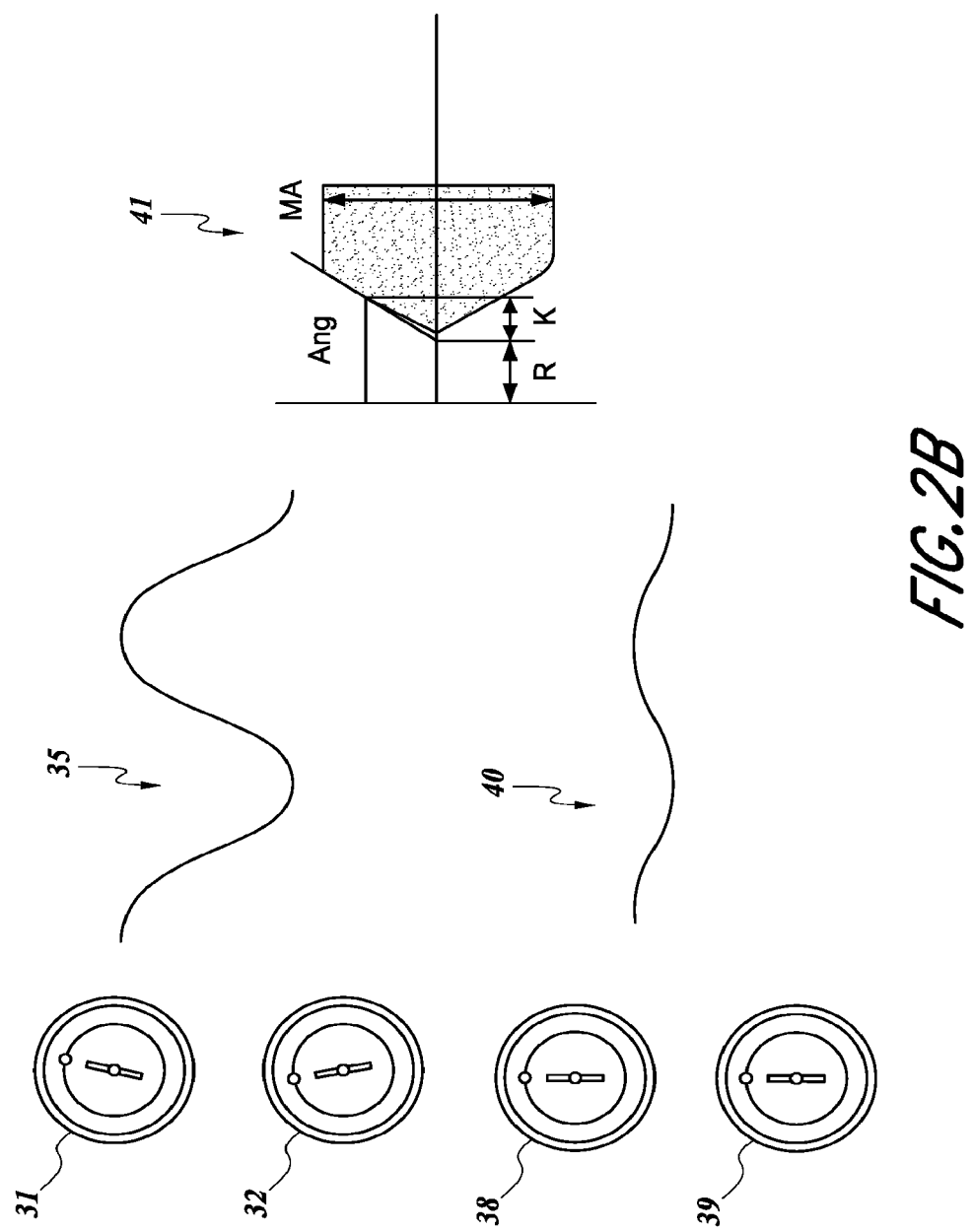
FIG. 2B are images describing translation of device motion into max amplitude (MA) profile.

The detailed translation of the device motion is shown in FIG. 2A. At the beginning of the measurement the disc motion is uninhibited and rotates the full range of motion, plus 4°45' 31 and minus 4°45' 32, in the fluid tested. This initial motion, before the onset of coagulation, is recorded as the baseline trace 35. The baseline trace is then differenced with the subsequent motion trace 36 to detect coagulation, which inhibits the coupling of motion of the magnet with the motion of the disc. In this embodiment, the displayed trace 36 (coagulation profile) is the difference between the baseline trace 35 and the subsequent motion trace 36. Prior to coagulation the baseline trace 35 is the same as the pre coagulation subsequent motion trace 36, and the coagulation profile 37 is the difference between the two: zero. As the blood coagulates, the induced motion is decoupled, and the magnetic field is no longer strong enough to overcome the viscoelasticity of the blood, as shown in FIG. 2B. Initially the motion is uninhibited 31, 32 producing the baseline motion 35. When coagulation occurs, decoupling reduces the induced motion 38, 39. Upon coagulation the large baseline trace 35 is differenced with the small post coagulation subsequent motion trace 40, resulting in a large amplitude profile 41. The moment in time shown, is at maximum amplitude represented by the parameter similar to the TEG parameter MA. As shown at the right of FIG. 2B and in FIG. 1B, the "reaction time" is the calculated time in decimal fractions of a second for a clot to reach 2 mm, "22 mm time" is the time in decimal fractions of a second for a clot to reach 22 mm, and "angle" is the slope of the angle between "reaction time" and "22 mm time". The "max clot" is maximum strength of a clot indicated in mm.

Figure 3:
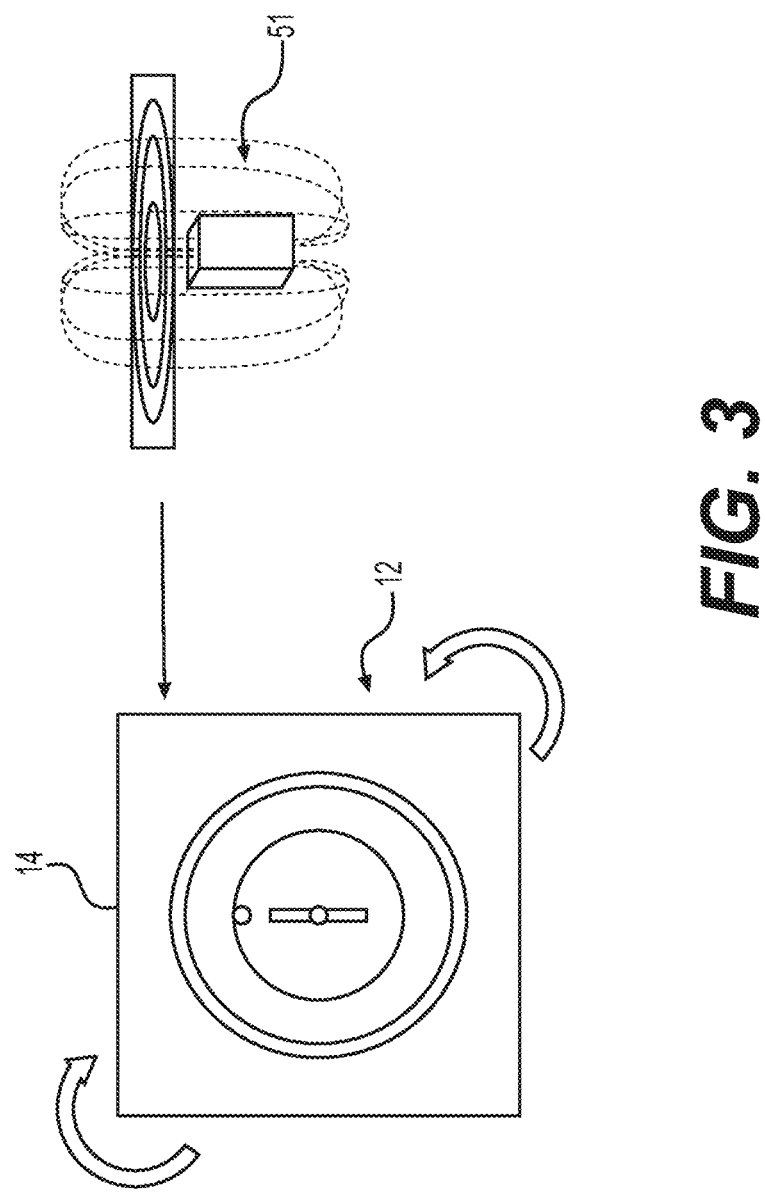
FIG. 3 shows an alternate embodiment with a fixed magnet.

A second embodiment of the BioMEMS device is shown in FIG. 3. In this embodiment a fixed magnet 51 is coupled to the disc. In this fixed magnet case, the rotation would be induced by rotating the cartridge 12 or well 14 within the cartridge. In this fixed magnet embodiment, the motion induced to the disc would be traced directly, with no differencing necessary. In this case the tracked motion could be directly used as the profile trace. Prior to the onset of coagulation there would be no motion coupled and the disc would oscillate uninhibited within the well. With no motion induced, the coagulation profile would be zero. In the fixed magnet case as the coagulation increases, the coupling would increase inducing more motion as coagulation continues. At MA the maximum amount of motion would be induced through the magnet.

Figure 4:
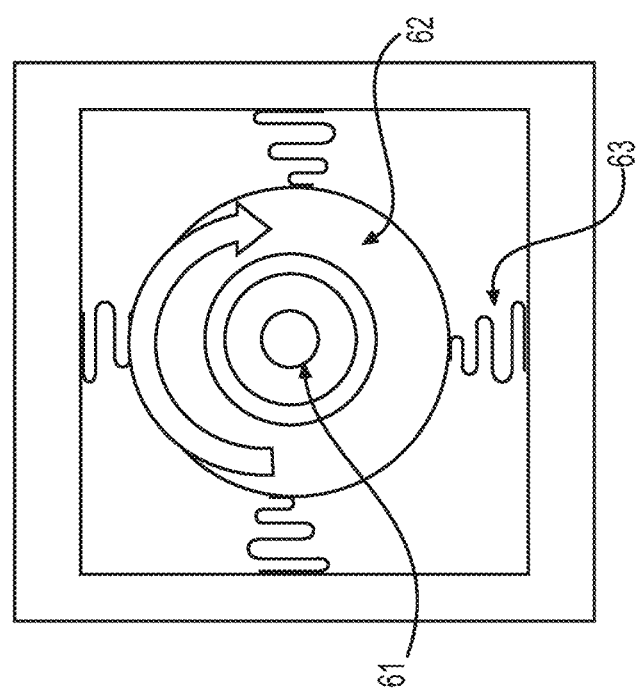
FIG. 4 shows an alternate embodiment with torsion springs.

A third embodiment of a coagulation profiling BioMEMS device is shown FIG. 4. This device has a center disc 61 and an outer ring 62 that is suspended by torsion springs 63. As the blood begins to coagulate, the rotating inner disc 61, actuated via an oscillating magnet, couples to the outer ring 62. This couples a reciprocating motion to the outer ring 2. At MA the maximum amount of motion would be induced through the magnet.

The BioMEMS embodiments shown are not all of the possible variations. For instance, one embodiment could use disc fixed to the center of the well and actuate a ferrous ring in the well. These variation of the described embodiments are apparent to one skilled in the art.

The measurement provided by the invention is impervious to motion. Due to the extremely small dimensions of the BioMEMS device, compared to the conventional size of TEG and ROTEM, the measurement is highly impervious to motion. The small mass of the device and small volume residing in the well present less inertia when external motion is applied. The ability to produce a noise-free measurement in the presence of motion is further enhanced by the magnetic coupling, which fixes the disc and the well in the magnetic field.

Figure 5:
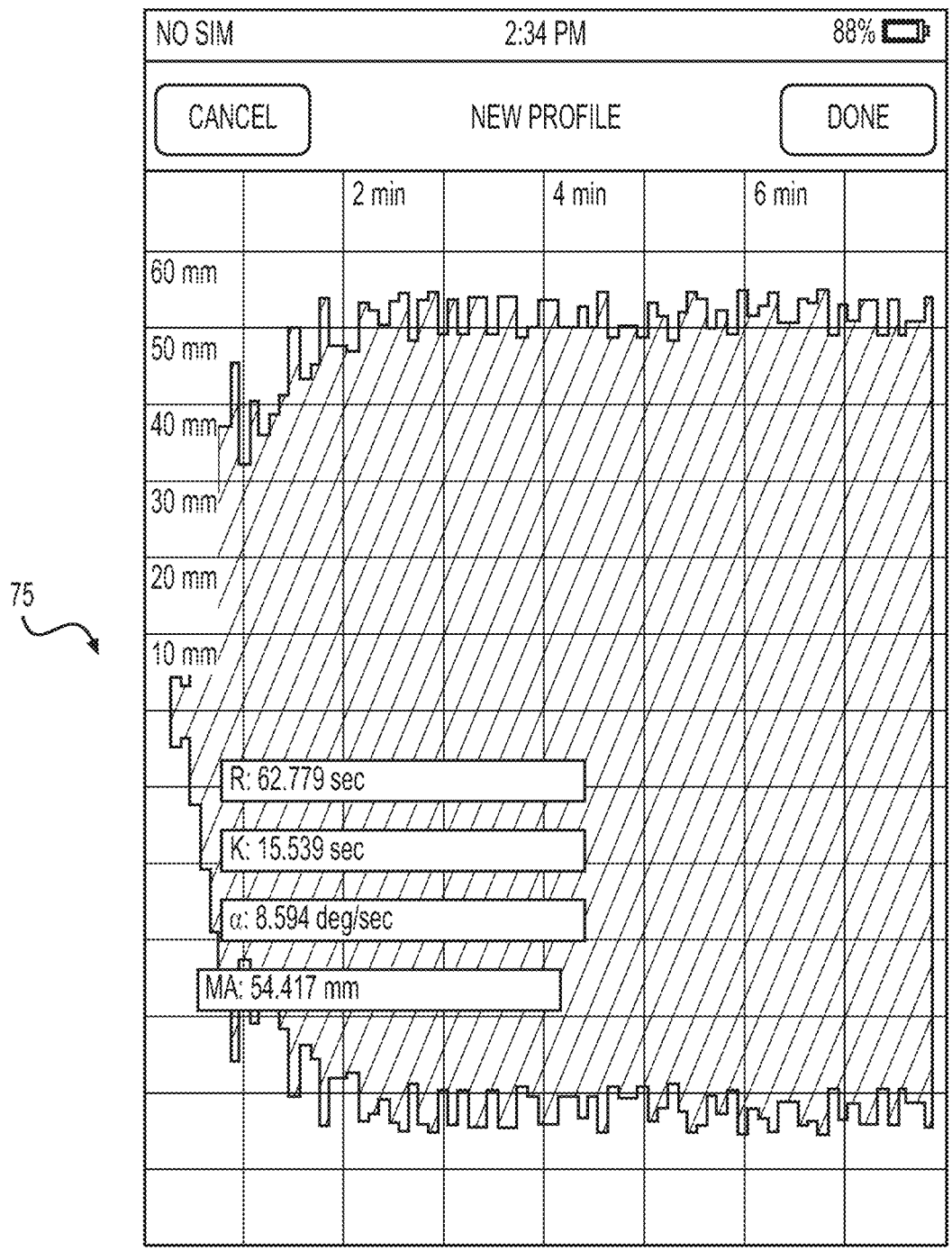
FIG. 5 is an image of a prototype showing accuracy of Level 1 control fluid.
Figure 6:
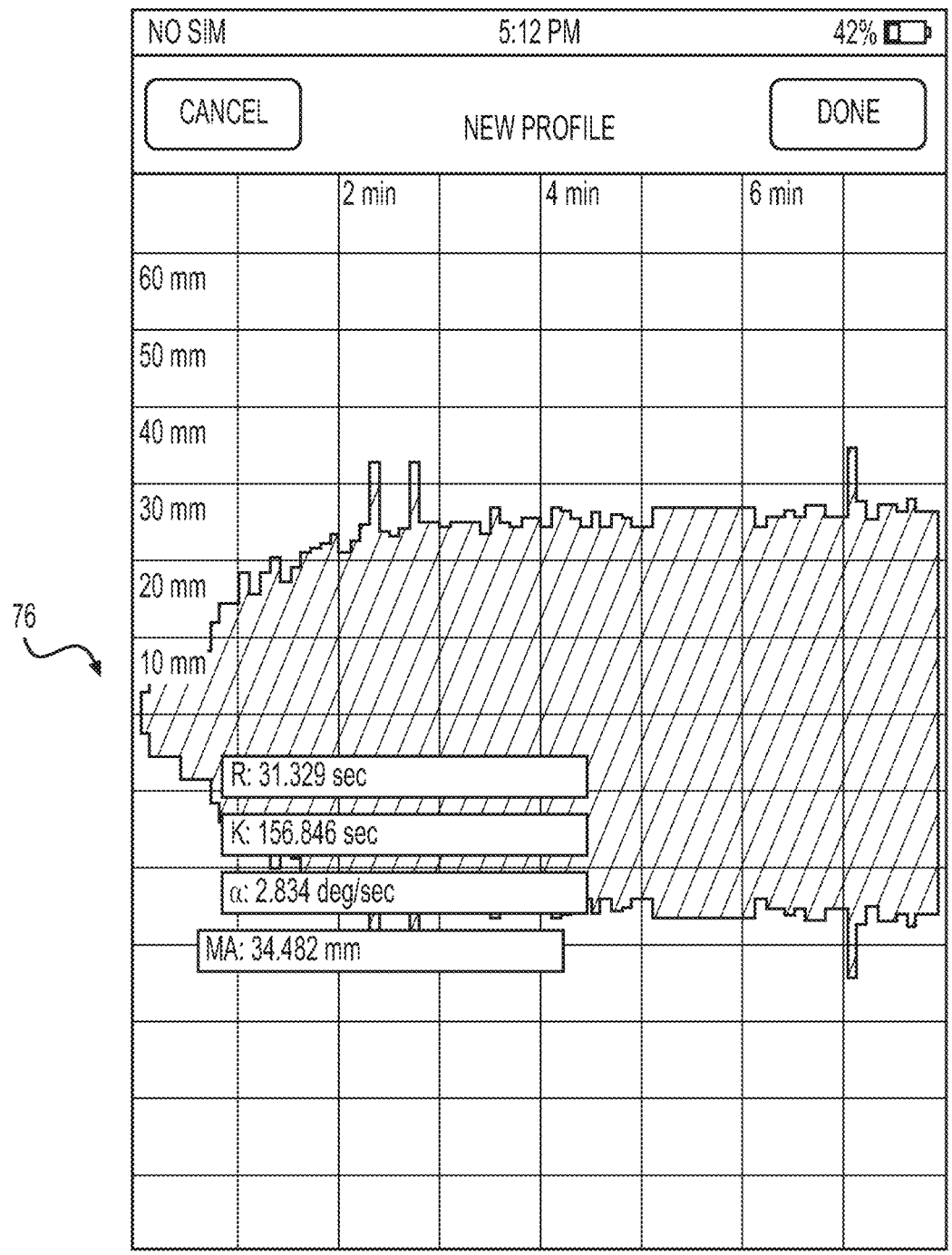
FIG. 6 is an image of a prototype showing accuracy of Level II control fluid.
Figure 7:
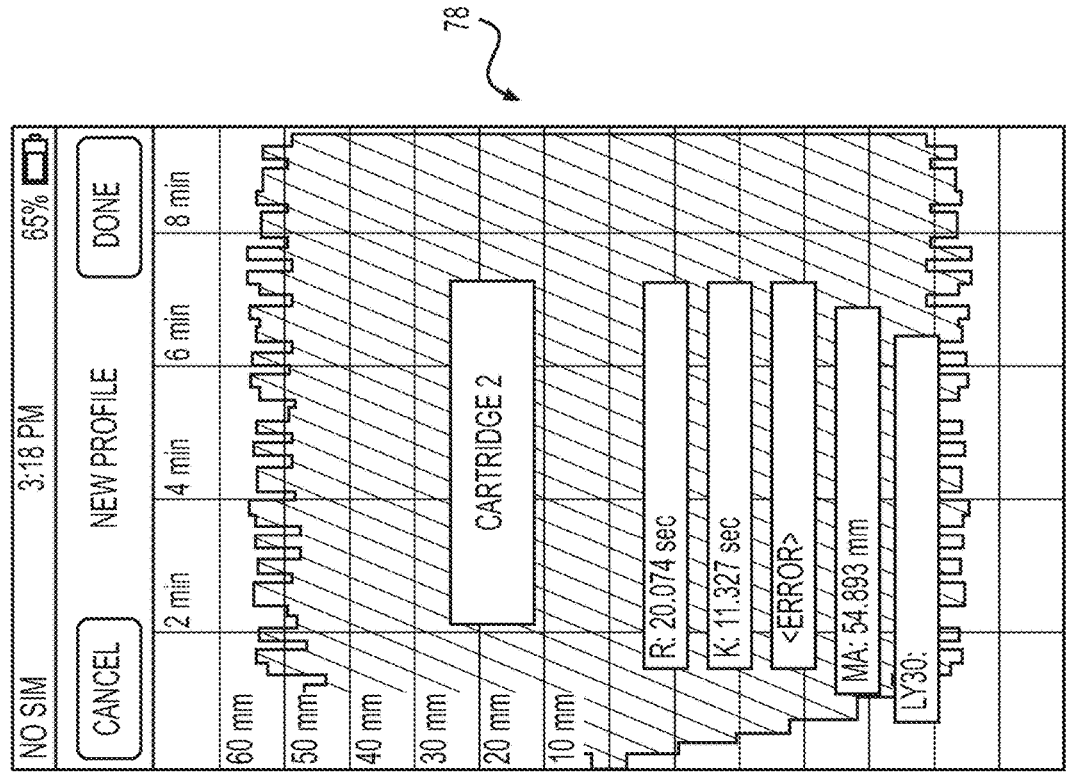
FIG. 7 is an image of a prototype showing repeatability of Level I profiles using two separate cartridges.
Figure 7:
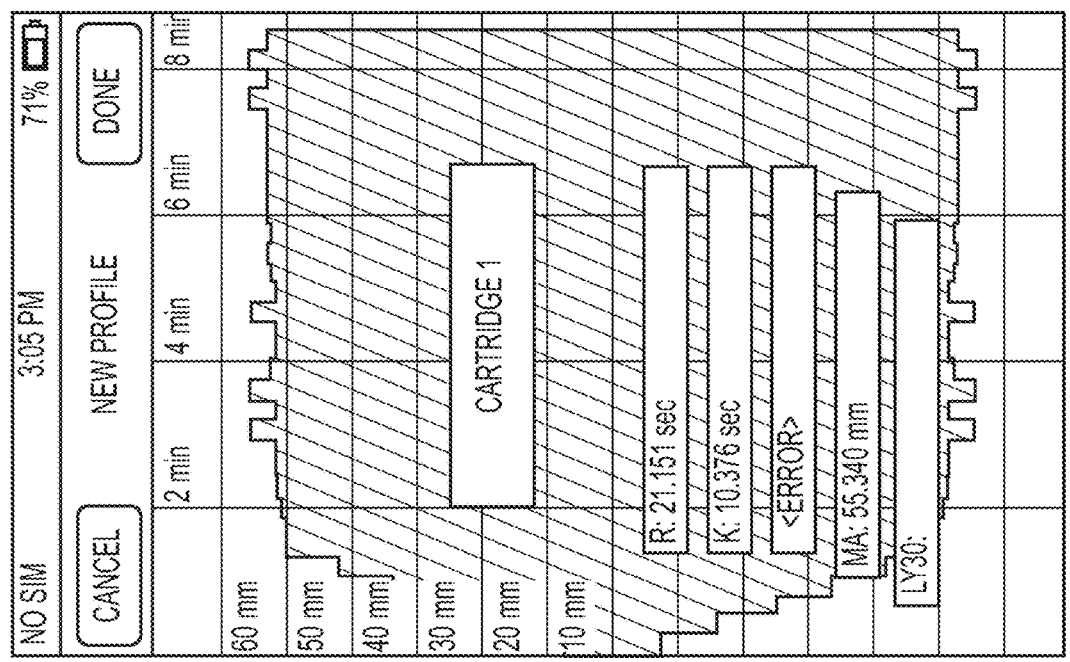

A prototype of the invention has provided concept validation. The image shown in FIG. 1B is an actual working prototype. The coagulation profile on the screen was taken using the prototype and shows the coagulation profile of using a quality control standard used and provided by Haemoscope, the makers of the TEG. The present prototype of the invention has accurately differentiated between the Haemoscope Level 1 control (normal profile) as shown in screen 75 in FIG. 5 and the Level II control (abnormal profile) as shown on screen in FIG. 6. In addition repeatability has been demonstrated with multiple cartridges accurately measuring the samples with nearly identical results, as shown on screens 77 and 78 in FIG. 7.

The polymer selection provides improved fibrin adhesion.

Figure 8:
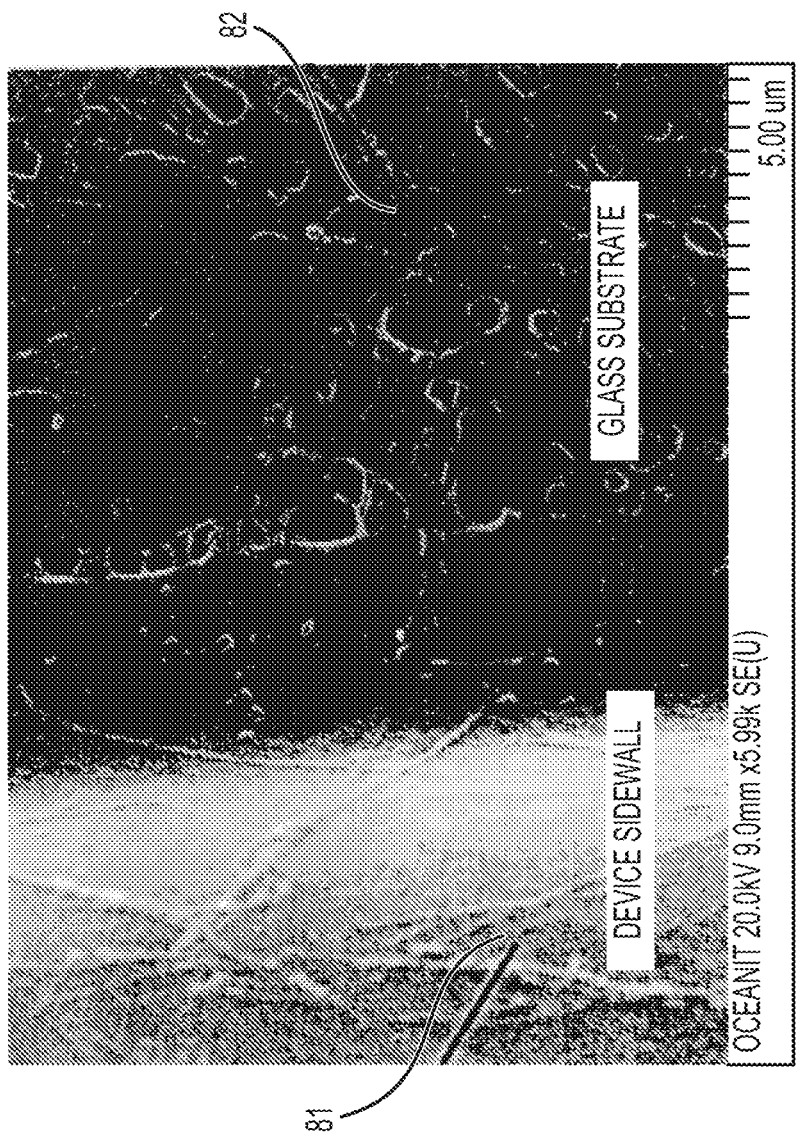
FIG. 8 is an SEM image showing fibrin adhesion into surface of HDDA.

The use of polymers for the fabrication of the cartridges has also been demonstrated to work well. In addition to being disposable and inexpensive to manufacture, the polymers have demonstrated advantages for us in this invention. Specifically, the use of HDDA promotes fibrinogen to be embedded into the polymer surface prior to the formation of fibrinogen. As the fibrinogen polymerizes it forms an excellent bond to the surfaces. This provides an ideal surface for detecting the viscoelasticity of the coagulating blood between the two HDDA surfaces. FIG. 8 shows fibrin 81 embedded into the surface of a HDDA disc sidewall. FIG. 8 also shows fibrin on the surface of the glass substrate, where air pockets are forming due to a lack of adhesion with no apparent fibrin embedded into the glass surface.

Figure 9:
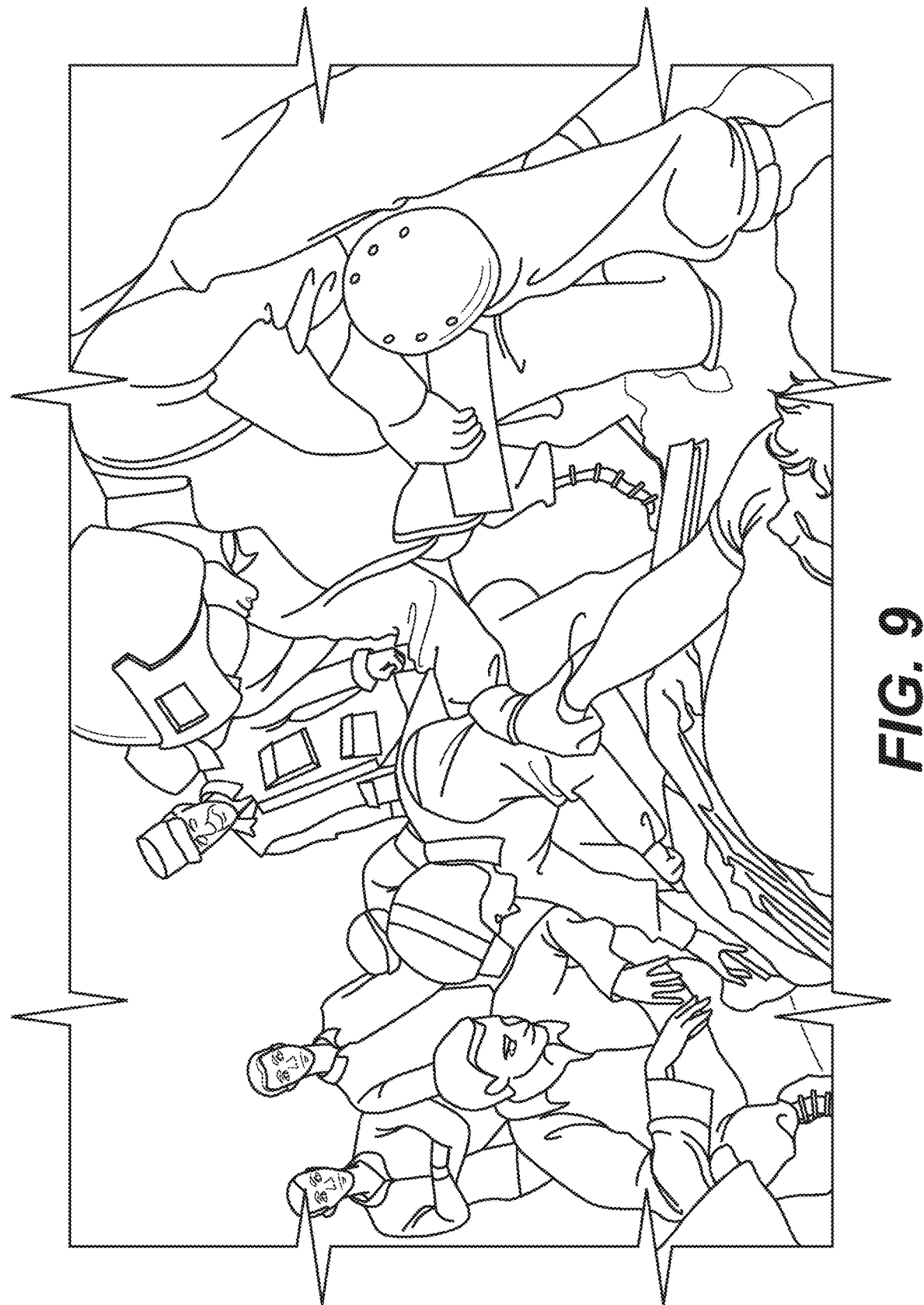
FIG. 9 shows a forward surgical team attending a soldier.

FIG. 9 shows a forward surgical team attending a soldier at a forward position where the present invention is needed. A similar case would be an EMT or paramedic attending a trauma victim.

Figure 10B:
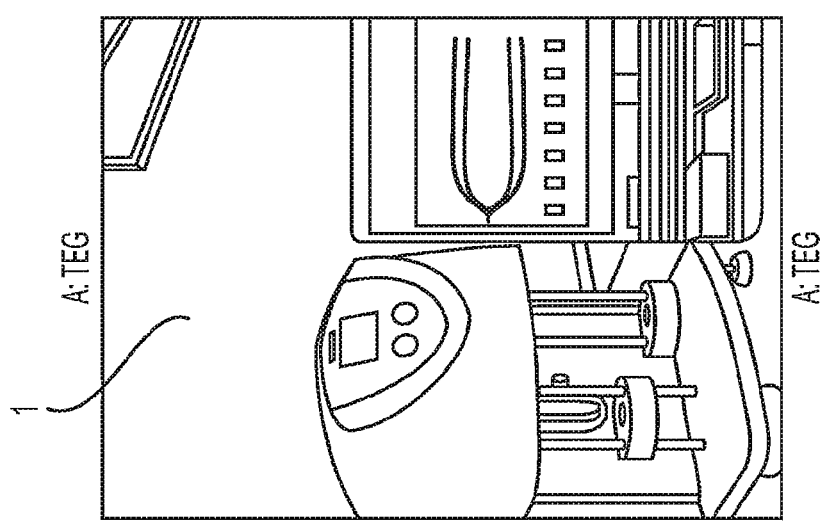
FIGS. 10A-10B show TEG and ROTEM.
Figure 10A:
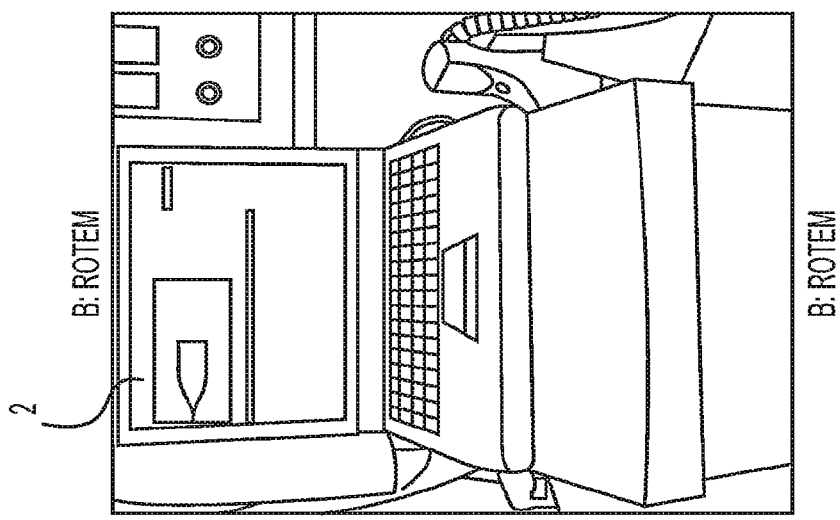

FIGS. 10A-10B show prior art TEG and ROTEM.

Figure 11B:
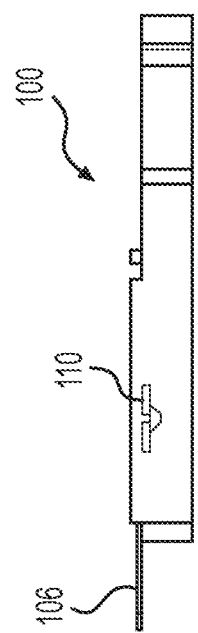
FIGS. 11A and 11B are perspective and a schematic side view showing a cartridge, platform, well, extended lid, an abutment on the platform and a disk attached to the lid, all of which are inserted in a receiver before fluid is injected into the well.
Figure 11A:
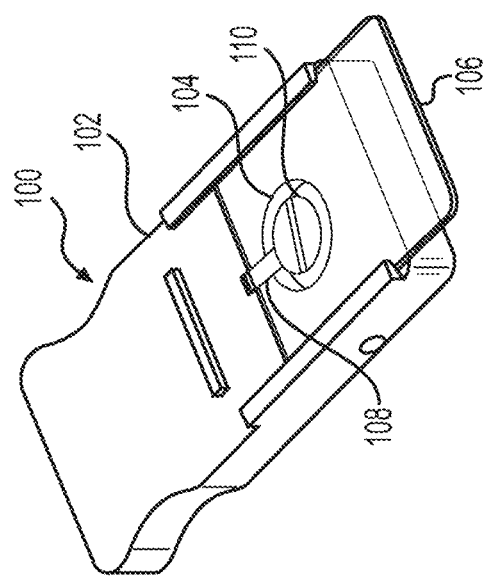

FIGS. 11A and 11B are perspective and a schematic side view showing additional features of the cartridge 100, a platform 102, a well 104, an extended lid 106, an abutment 108 on the platform and a disk 110 attached to the lid 108, all of which are inserted in a receiver before fluid is injected into the well 104. FIG. 11B is a schematic representation of the well 104 and the disk 110 which is still attached to a bottom of the lid 106.

FIGS. 12A and 12B are perspective and a schematic side view showing disk loading technique of the cartridge 100, platform 102, the well 104, the extended lid 106, and an abutment 108 on the platform. Disk 110 is still attached to the lid 106.

Figure 13B:
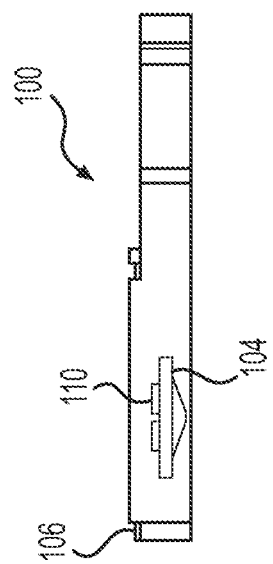
FIGS. 13A and 13B are perspective and a schematic side view showing a cartridge, platform, well, lid, an abutment on the platform and a disk attached to the lid, fluid is injected into the well after the lid is pushed back and the disk is dropped from the lid into the well.
Figure 13A:
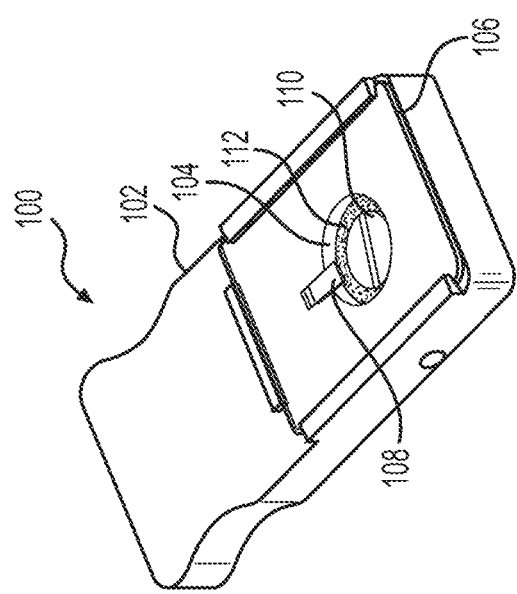

FIGS. 13A and 13B are perspective and a schematic side view showing a cartridge 100, the platform 102, well 104 and lid 106. An abutment 108 on the platform 102 has dislodged disk 110 from the lid after fluid is injected into the well and after lid 106 is pushed back and disk 110 is dislodged and dropped from the lid into the well.

Figure 14:
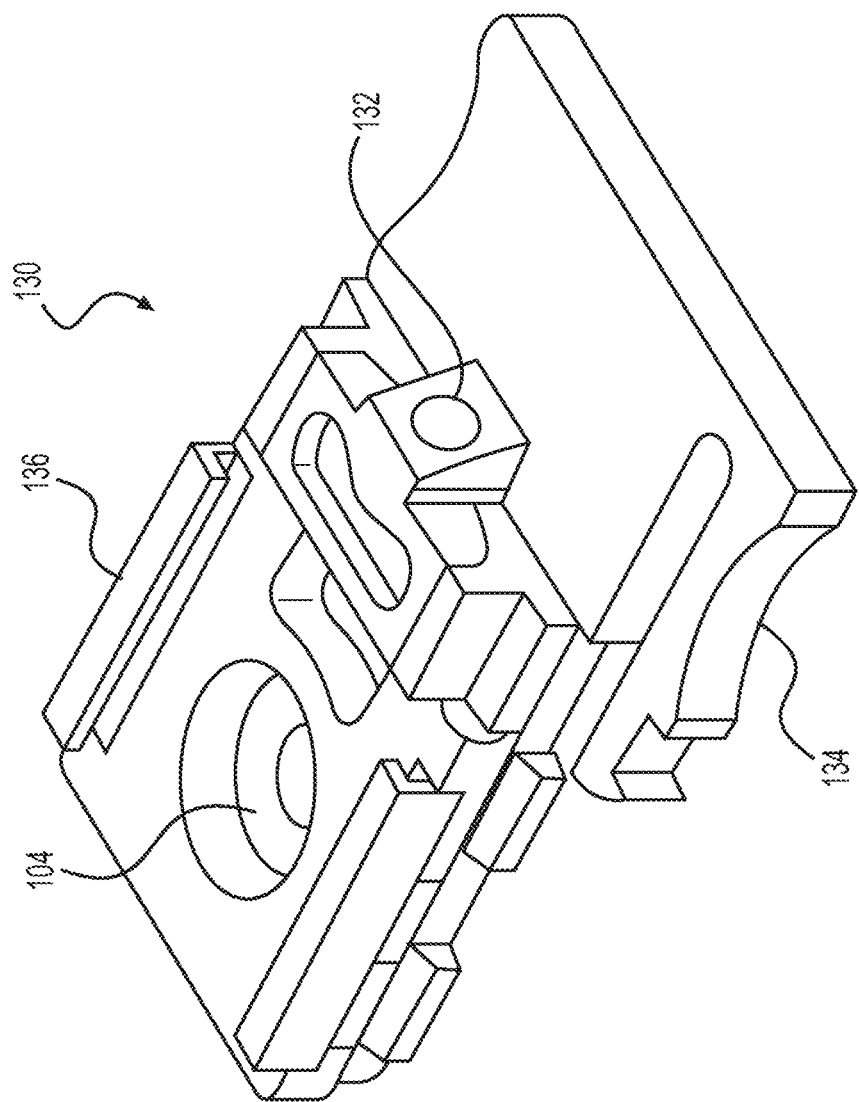
FIG. 14 is a perspective view of a cartridge without a cover showing a fluid injection port at one end of a passageway to the well and a retaining clip for retaining the cartridge in the receiver.

FIG. 14 is a perspective view of a cartridge 130, which shows additional features of an injection port and a retaining clip. In this case it is shown without a lid, showing a fluid injection port 132 at one end of a passageway to the well and retaining clip 134 for retaining the cartridge in the receiver. Upward and inward extending opposite guide rails 136 hold a lid 106.

Figure 15:
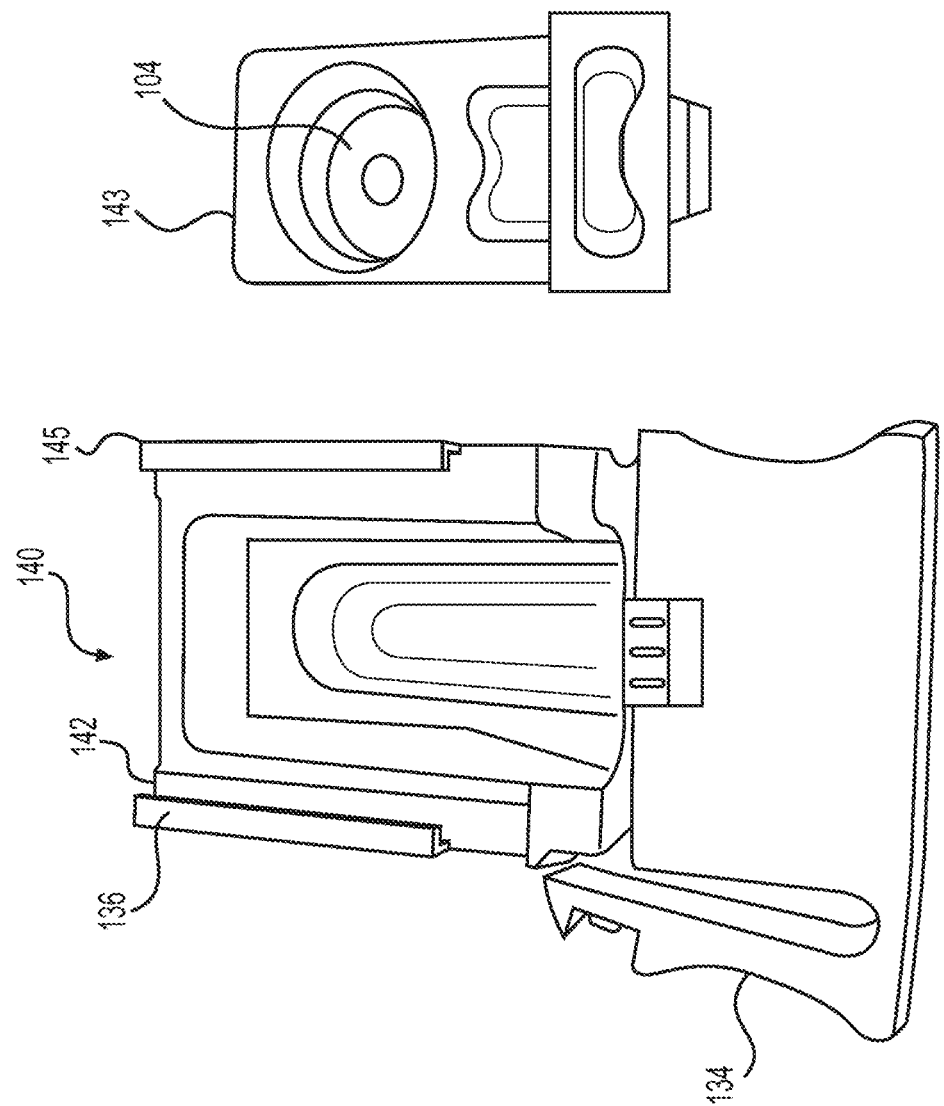
FIG. 15 shows a two-piece injection construction of the cartridge platform for compatibility with manufacture by injection molding.

FIG. 15 shows a two-piece injection construction of a cartridge 140 platform 142 for compatibility with manufacture by injection molding. Inner part 143 holds the well 104, and outer part 145 has the retaining clip 134 and the guide rails 136.

While the invention has been described with reference to specific embodiments, modifications and variations of the invention may be constructed without departing from the scope of the invention, which is defined in the following claims.

We claim:

1. A method comprising:
    turning a disc in a first direction and a second direction opposite the first direction in an oscillating motion within a liquid capable of coagulating, wherein the disc comprises a first tracking point at the rotational center of the disc, wherein the disc comprises a second tracking point located at a distance from the rotational center of the disc; and
    tracking the oscillating motion of the first tracking point and the second tracking point of the disc to generate a coagulation profile, wherein the oscillating motion changes over time as the liquid coagulates.

2. The method of claim 1, further comprising identifying a coagulation abnormality.

3. The method of claim 1, further comprising plotting the change in motion to show an amplitude over time.

4. The method of claim 1, wherein the oscillating motion is induced externally using a magnetic field.

5. The method of claim 1, wherein the oscillating motion is actuated using a mechanical drive.

6. The method of claim 1, wherein the oscillating motion is actuated using a spring.

7. The method of claim 1, wherein the coagulation profile is displayed to a user on a screen.

8. The method of claim 1, wherein the coagulation profile is stored.

9. The method of claim 1, further comprising sending the coagulation profile to a remote location.

10. A method comprising:
    turning a disc in a first direction and a second direction opposite the first direction in an oscillating motion in a liquid capable of coagulating, wherein the disc comprises a first tracking point located at a rotational center of the disc, wherein the disc comprises a second tracking point located at a distance from the rotational center of the disc; and
    tracking the oscillating motion of the first tracking point and the second tracking point of the disc while the liquid coagulates, wherein the disc oscillates in a specific rotational pattern.

11. The method of claim 10, wherein the oscillating motion is tracked with a video camera.

12. The method of claim 10, wherein the specific rotational pattern comprises a rotation of +/−4° 45'.

13. The method of claim 10, wherein the specific rotational pattern comprises rotation over five seconds.

14. The method of claim 10, wherein the specific rotational pattern comprises rotation over ten seconds.

15. The method of claim 10, wherein a motor or server turns a magnet to provide magnetic actuation.

16. The method of claim 10, wherein the oscillating motion is induced externally using a mechanical inducer of rotation.

17. The method of claim 10, wherein the oscillating motion is induced externally using an electrostatic inducer of motion.

18. A method for measuring coagulation, comprising:
    turning a disc in a first direction and a second direction opposite the first direction in an oscillating motion within a liquid capable of coagulating, wherein the disc comprises a first tracking point proximate the rotational center of the disc, wherein the disc comprises a second tracking point located at a distance from the rotational center of the disc; and
    tracking the oscillating motion of the second tracking point of the disc to generate a coagulation profile, wherein the coagulation profile is configured to facilitate evaluation of coagulation abnormalities.

19. The method of claim 18, wherein the disc and liquid are disposed within a well of a cartridge, wherein the cartridge is disposed within an handheld medical analyzer.

20. The method of claim 18, wherein the coagulation profile is generated in an ambulance.

* * * * *